United States Patent
Akahori

(10) Patent No.: US 9,947,094 B2
(45) Date of Patent: Apr. 17, 2018

(54) MEDICAL IMAGE PROCESSING DEVICE, OPERATION METHOD THEREFOR, AND MEDICAL IMAGE PROCESSING PROGRAM

(71) Applicant: FUJIFILM Corporation, Tokyo (JP)

(72) Inventor: Sadato Akahori, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 93 days.

(21) Appl. No.: 15/092,164

(22) Filed: Apr. 6, 2016

(65) Prior Publication Data

US 2016/0217572 A1 Jul. 28, 2016

Related U.S. Application Data

(63) Continuation of application No. PCT/JP2014/005103, filed on Oct. 7, 2014.

(30) Foreign Application Priority Data

Oct. 11, 2013 (JP) .................................. 2013-213659

(51) Int. Cl.
*G06T 7/00* (2017.01)
*A61B 5/055* (2006.01)
(Continued)

(52) U.S. Cl.
CPC .......... *G06T 7/0014* (2013.01); *A61B 5/0044* (2013.01); *A61B 5/055* (2013.01); *A61B 6/03* (2013.01); *A61B 6/032* (2013.01); *A61B 6/503* (2013.01); *A61B 6/5294* (2013.01); *G06K 9/6212* (2013.01); *G06T 5/008* (2013.01); *G06T 7/11* (2017.01); *G06T 7/187* (2017.01);
(Continued)

(58) Field of Classification Search
CPC combination set(s) only.
See application file for complete search history.

(56) References Cited

U.S. PATENT DOCUMENTS 6,021,213 A * 2/2000 Helterbrand .............. G06T 7/11
382/128
6,430,430 B1 * 8/2002 Gosche ................. G06T 7/0012
128/920
(Continued)

FOREIGN PATENT DOCUMENTS

JP 64-74678 A 3/1989
JP 3-236830 A 10/1991
(Continued)

OTHER PUBLICATIONS

Delong et al., "Globally Optimal Segmentation of Multi-Region Objects", In International Conference on Computer Vision (ICCV), Kyoto, Oct. 2009, pp. 1-8.
(Continued)

*Primary Examiner* — Tsung-Yin Tsai
(74) *Attorney, Agent, or Firm* — Birch, Stewart, Kolasch & Birch, LLP

(57) ABSTRACT

There are provided a feature point extraction unit that extracts an anatomical feature point included in a medical image based on the medical image and a standardization conditions acquisition unit that acquires standardization conditions of pixel values of the medical image based on some pixel values around the anatomical feature point among the pixel values of the medical image.

16 Claims, 6 Drawing Sheets

(51) Int. Cl.
| | |
|---|---|
| *A61B 5/00* | (2006.01) |
| *A61B 6/03* | (2006.01) |
| *A61B 6/00* | (2006.01) |
| *G06K 9/62* | (2006.01) |
| *G06T 5/00* | (2006.01) |
| *G06T 7/11* | (2017.01) |
| *G06T 7/187* | (2017.01) |

(52) U.S. Cl.
CPC .............. *A61B 2576/023* (2013.01); *G06T 2207/10072* (2013.01); *G06T 2207/10081* (2013.01); *G06T 2207/10088* (2013.01); *G06T 2207/30048* (2013.01); *G06T 2207/30101* (2013.01); *G06T 2210/41* (2013.01)

(56) References Cited

U.S. PATENT DOCUMENTS

| | | | |
|---|---|---|---|
| 7,599,539 | B2 | 10/2009 | Kunz et al. |
| 8,884,618 | B2* | 11/2014 | Mahfouz ............... A61F 2/3094 324/309 |
| 2006/0182363 | A1 | 8/2006 | Jellus |
| 2008/0021502 | A1* | 1/2008 | Imielinska ............. A61B 6/032 607/1 |
| 2009/0257628 | A1* | 10/2009 | Ranga .................. G06K 9/6807 382/128 |
| 2011/0172516 | A1 | 7/2011 | Sugiura |
| 2012/0093385 | A1* | 4/2012 | Yokosawa ............ A61B 5/0037 382/131 |
| 2013/0083982 | A1 | 4/2013 | Nakamura |
| 2014/0303481 | A1* | 10/2014 | Sorensen ............... A61B 5/055 600/410 |
| 2015/0050218 | A1* | 2/2015 | Giavazzi .............. A61K 49/085 424/9.3 |
| 2015/0356730 | A1* | 12/2015 | Grove .................. G01N 23/046 382/124 |

FOREIGN PATENT DOCUMENTS

| | | |
|---|---|---|
| JP | 2004-141612 A | 5/2004 |
| JP | 2006-175231 A | 7/2006 |
| JP | 2010-227394 A | 10/2010 |
| JP | 2011-143055 A | 7/2011 |
| JP | 2013-75079 A | 4/2013 |

OTHER PUBLICATIONS

Etoh, "Survey of Snakes, Active Contour Models", Medical Imaging Technology, Jan. 1994, vol. 12, No. 1, pp. 9-15.
International Search Report for PCT/JP2014/005103 dated Jan. 27, 2015.
Kass et al., "Snakes: Active Contour Models", International Journal of Computer Vision, 1988, vol. 1, pp. 321-331.
Written Opinion of the International Searching Authority for PCT/JP2014/005103 (PCT/ISA/237) dated Jan. 27, 2015.

* cited by examiner

MEDICAL IMAGE BEFORE CONVERSION PROCESSING

CONVERSION IMAGE

MEDICAL IMAGE PROCESSING DEVICE, OPERATION METHOD THEREFOR, AND MEDICAL IMAGE PROCESSING PROGRAM

CROSS REFERENCE TO RELATED APPLICATIONS

The present application is a Continuation of PCT International Application No. PCT/JP2014/005103 filed on Oct. 7, 2014, which claims priority under 35 U.S.C. § 119(a) to Japanese Patent Application No. 2013-213659 filed on Oct. 11, 2013. Each of the above applications is hereby expressly incorporated by reference, in its entirety, into the present application.

BACKGROUND OF THE INVENTION

1. Field of the Invention

The present invention relates to a medical image processing device, method, and program for acquiring the standardization conditions for correcting the variation in the signal level or the contrast of an image based on a medical image.

2. Description of the Related Art

Conventionally, various methods for acquiring a tomographic image of a subject or a three-dimensional image formed of tomographic images and extracting an anatomical region, such as the left ventricle of the heart, from the tomographic image or the like using a computed tomography (CT) apparatus, a magnetic resonance imaging (MRI) apparatus, an ultrasound imaging apparatus, or the like have been proposed.

Specifically, for example, in the case of a three-dimensional image captured by a CT apparatus, a desired region can be extracted with a certain degree of accuracy by threshold value processing for pixel values. For example, it is possible to extract a lung field region by extracting pixels having low pixel values, or it is possible to extract a bone region or an angiographic region by extracting pixels having high pixel values. Accordingly, it is possible to use the information of pixel values as a reliable feature.

SUMMARY OF THE INVENTION

However, although there are a T1-weighted image in which a difference between T1 values (longitudinal relaxation time) of the tissue is emphasized, a T2-weighted image in which a difference between T2 values (transverse relaxation time) of the tissue is emphasized, and the like as images captured by an MRI apparatus, the quality of these images changes greatly with the magnetic field strength or the pulse sequence. In addition, unlike a CT image in which pixel values are defined by substances (for example, air is −1000, water is 0, and hard bone is +1000), pixel values are not standardized.

Therefore, in the case of an MR image, there is no choice but to rely on the shape or contrast between pixels at the time of region extraction. For this reason, it is difficult to accurately perform automatic extraction or semi-automatic extraction.

In addition, in the case of a CT image, if an appropriate window width and window level or a color map is set according to a diagnostic target part, it is possible to observe an image in a state in which each anatomical structure is assigned with a fixed brightness or color.

In the case of an MR image, however, since pixel values are not standardized as described above, it is necessary to adjust the setting of the window width and the window level or the color map for each imaging in order to observe an image in a desired state. Accordingly, there is a problem that a time for this adjustment is required.

JP2013-75079A proposes a method of extracting a ventricular region using the graph cut method. However, only the method of using a CT value is disclosed.

JP2004-141612A proposes a method of extracting a ventricular region using a result binarized based on a threshold value set in advance. However, in the case of the above-described MR image, it is not possible to perform accurate region extraction using the method disclosed in JP2004-141612A since the pixel values are not standardized.

JP2006-175231A proposes a method of correcting non-uniformity of an MR image using a High-pass filter. However, it is not possible to correct a variation in the signal level or the contrast of the entire image.

In view of the aforementioned situation, it is an object of the present invention to provide a medical image processing device, an operation method therefor, and a medical image processing program capable of accurately extracting an anatomical region from a medical image in which pixel values are not standardized as an MR image and capable of reducing a variation in the pixel values or the contrast of each medical image.

A medical image processing device of the present invention includes: a feature point extraction unit that extracts an anatomical feature point included in a medical image based on the medical image; and a standardization conditions acquisition unit that acquires standardization conditions of pixel values of the medical image based on some pixel values around the anatomical feature point among the pixel values of the medical image.

In the medical image processing device of the present invention described above, the standardization conditions acquisition unit can acquire pixel values of a pixel group around the anatomical feature point, acquire a statistical quantity of the pixel values of the pixel group, and acquire standardization conditions based on the statistical quantity.

The standardization conditions acquisition unit can classify the pixel values of the pixel group into a plurality of groups, acquire a statistical quantity of each of the groups, and acquire the standardization conditions based on the statistical quantity.

The standardization conditions acquisition unit can acquire the standardization conditions in which the statistical quantity of the pixel values of the pixel group is a value set in advance.

The standardization conditions acquisition unit can acquire a boundary value for classifying the pixel group into a plurality of groups and acquire the standardization conditions based on the boundary value.

The feature point extraction unit can generate a conversion image by performing conversion processing on each pixel value of the medical image based on a statistical quantity, which is calculated based on pixel values around each pixel value, and extract the anatomical feature point based on the conversion image.

In addition, it is possible to provide a region extraction processing unit that performs region extraction processing for extracting an anatomical region included in the medical image based on the standardization conditions and the medical image.

The region extraction processing unit can perform the region extraction processing by setting an evaluation function based on the standardization conditions and the medical image and calculating an optimal solution of the evaluation function.

It is possible to provide a standardization processing unit that performs standardization processing on the medical image using the standardization conditions.

It is possible to provide a display control unit that displays a medical image having been subjected to the standardization processing.

The display control unit can set a window width and a level value based on the standardization conditions.

It is possible to provide a display control unit that generates a display image by performing processing including both the standardization conditions and display conditions directly on the medical image and displays the display image.

As the medical image, it is possible to use a medical image captured by a magnetic resonance imaging (MRI) apparatus.

An operation method of a medical image processing device of the present invention is an operation method of a medical image processing device including a feature point extraction unit and a standardization conditions acquisition unit. The operation method of a medical image processing device of the present invention includes: extracting an anatomical feature point included in a medical image based on the medical image using the feature point extraction unit; and acquiring standardization conditions of pixel values of the medical image based on some pixel values around the anatomical feature point among the pixel values of the medical image using the standardization conditions acquisition unit.

A medical image processing program of the present invention causes a computer to function as: a feature point extraction unit that extracts an anatomical feature point included in a medical image based on the medical image; and a standardization conditions acquisition unit that acquires standardization conditions of pixel values of the medical image based on some pixel values around the anatomical feature point among the pixel values of the medical image.

According to the medical image processing device, the operation method therefor, and the medical image processing program of the present invention, an anatomical feature point included in a medical image is extracted based on the medical image, and the standardization conditions of the pixel values of the medical image are acquired based on some pixel values around the anatomical feature point among the pixel values of the medical image. Therefore, in the case of standardizing an MR image, an ultrasound image, or the like based on the standardization condition, it is possible to accurately extract an anatomical region from these medical images and to reduce a variation in the pixel values or the contrast of each medical image. In addition, since the standardization conditions are acquired based on some pixel values around the anatomical feature point, it is possible to acquire more appropriate standardization conditions corresponding to the anatomical structure.

DESCRIPTION OF THE PREFERRED EMBODIMENTS

Figure 1:
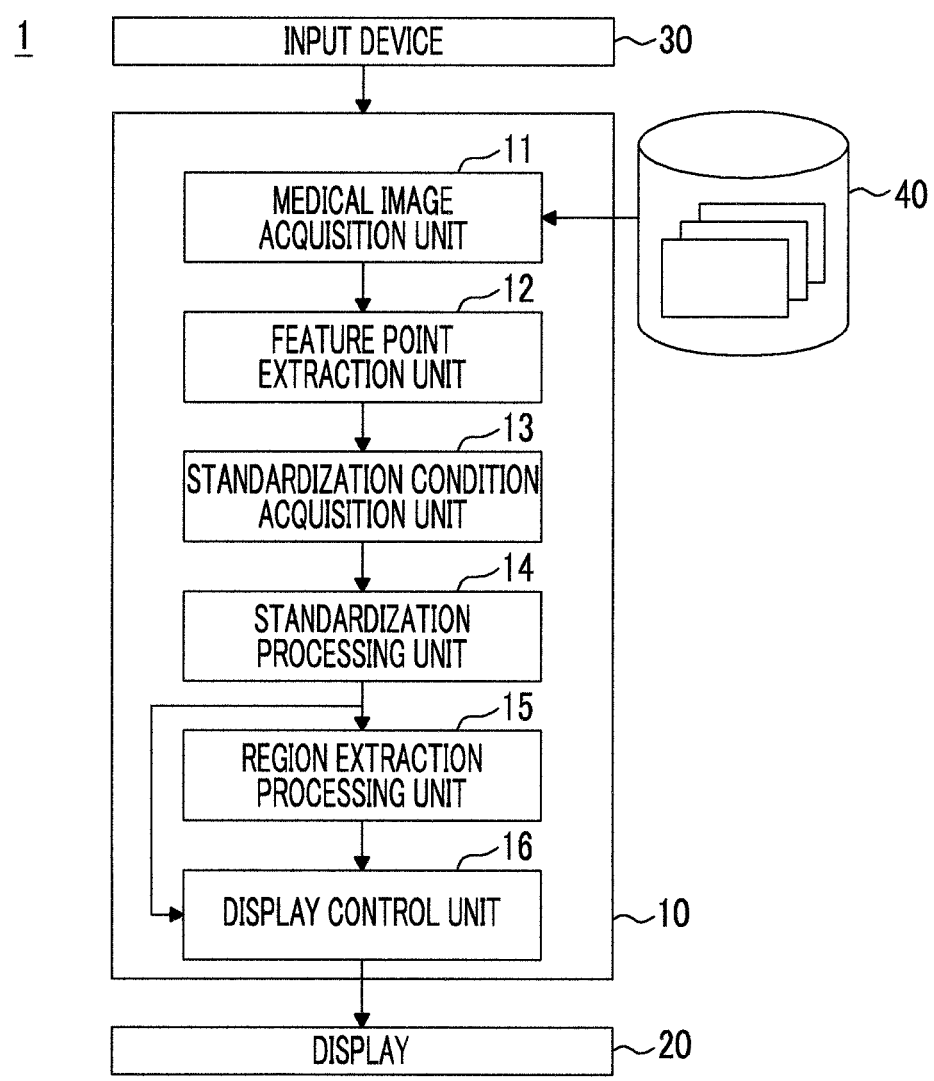
FIG. 1 is a block diagram showing the schematic configuration of a medical image diagnosis support system using an embodiment of a medical image processing device, an operation method therefor, and a medical image processing program of the present invention.

Hereinafter, a medical image diagnosis support system using an embodiment of a medical image processing device, method, and program of the present invention will be described in detail with reference to the diagrams. FIG. 1 is a block diagram showing the schematic configuration of the medical image diagnosis support system using the present embodiment.

As shown in FIG. 1, a medical image diagnosis support system 1 of the present embodiment includes a medical image processing device 10, a display 20, an input device 30, and a medical image storage server 40.

The medical image processing device 10 is formed by installing the medical image processing program of the present embodiment in a computer. The medical image processing device 10 includes a central processing unit (CPU), a semiconductor memory, and a storage device, such as a hard disk or a solid state drive (SSD) in which the medical image processing program of the present embodiment is installed. By these hardware components, a medical image acquisition unit 11, a feature point extraction unit 12, a standardization conditions acquisition unit 13, a standardization processing unit 14, a region extraction processing unit 15, and a display control unit 16 that are shown in FIG. 1 are formed. Each of the units described above is operated by the medical image processing program installed in the hard disk that is executed by the central processing unit. A medical image processing program recorded on a recording medium, such as a CD-ROM, may be used, or a medical image processing program downloaded from a server or the like through the Internet may be used, or a medical image processing program provided by Software as a Service (SaaS) through the Internet may be used.

The medical image acquisition unit 11 acquires a medical image captured in advance. In the present embodiment, tomographic images obtained by imaging parts including the heart using a Magnetic Resonance Imaging (MRI) apparatus or volume data reconstructed from the tomographic image is acquired as medical images. Medical images are stored in the medical image storage server 40 in advance together with the identification information of the subject, and the medical image acquisition unit 11 reads a medical image corresponding to the identification information of the subject, which is input through the input device 30, from the medical image storage server 40.

The feature point extraction unit 12 extracts an anatomical feature point based on the medical image acquired by the medical image acquisition unit 11. It is preferable that the anatomical feature point is a point showing invariable features that the body always has in the anatomy of the body. In the present embodiment, the center point of the left ventricle of the heart is extracted.

Here, the method of extracting the center point of the left ventricle of the heart in the feature point extraction unit 12 of the present embodiment will be described.

Figure 2:
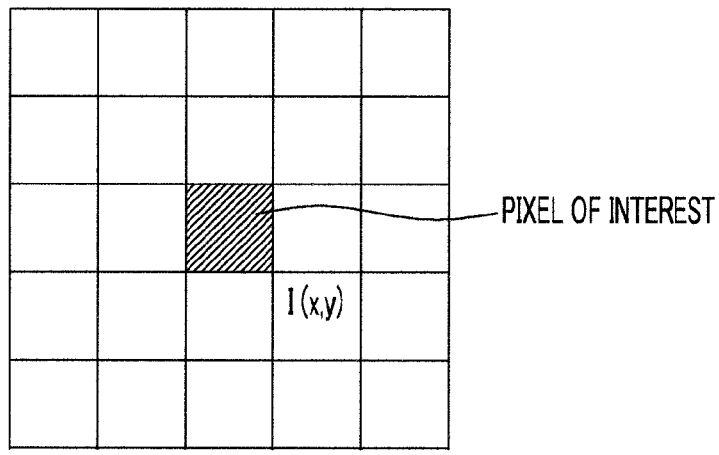
FIG. 2 is a diagram showing an example of a kernel used when generating a conversion image.

First, the feature point extraction unit 12 generates a conversion image by performing conversion processing on each pixel value of the input medical image based on the statistical quantity that is calculated based on the surrounding pixel values. Specifically, for a predetermined pixel of interest I(x, y) in a medical image, an average value Mlocal and a standard deviation SDlocal in the kernel of 5 pixels×5 pixels shown in FIG. 2 are calculated. By performing conversion processing using the following Equation (1), Ic(x, y) is calculated. In the following Equation, Const is a constant set in advance. Then, Ic(x, y) is calculated with each pixel included in the medical image as a pixel of interest, and a conversion image formed of Ic(x, y) is generated.

$$Ic(x,y)=(I(x,y)-Mlocal)\times Const/SDlocal \quad (1)$$

Figure 3A:
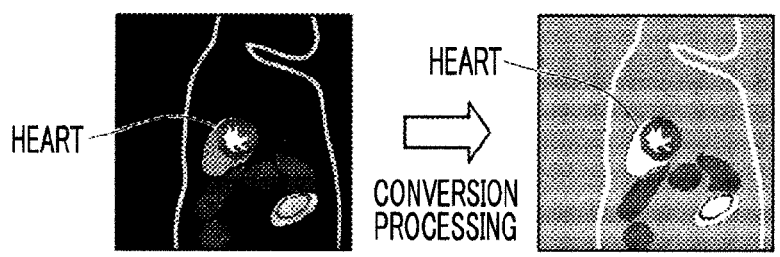
FIGS. 3A and 3B are diagrams showing examples of a medical image before conversion processing and a medical image after conversion processing.
Figure 3B:
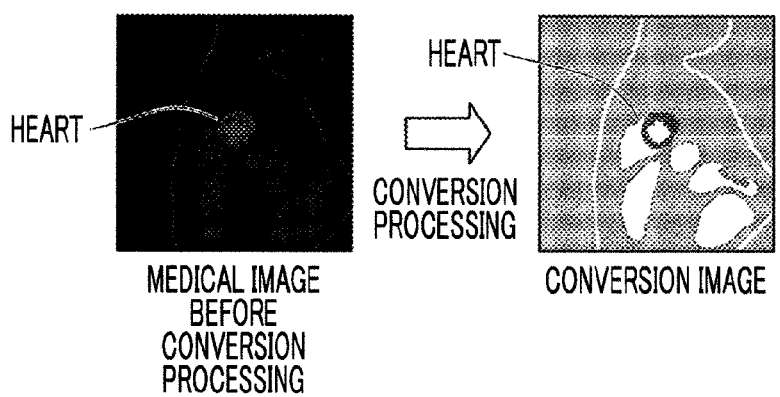

FIGS. 3A and 3B show examples of medical images before the conversion processing described above and examples of conversion images after the conversion processing. The medical images before the conversion processing in FIGS. 3A and 3B are medical images captured under different imaging conditions or the like. Therefore, the medical images before the conversion processing in FIGS. 3A and 3B are images having completely different contrasts. By performing the above-described conversion processing on these medical images, it is possible to have the features of the local structure regardless of the variation in the pixel values or the contrast of the original medical image. Therefore, in the anatomical feature point extraction processing to be described later, it is possible to perform stable extraction processing.

Then, the feature point extraction unit 12 extracts a left ventricle center point from the above-described conversion image as an anatomical feature point. Specifically, first, a sample group of the heart including the left ventricle center point and a sample group including no left ventricle center point are prepared in advance, and a discriminator is created according to a machine learning method based on Adaboost using these sample groups.

Figure 4:
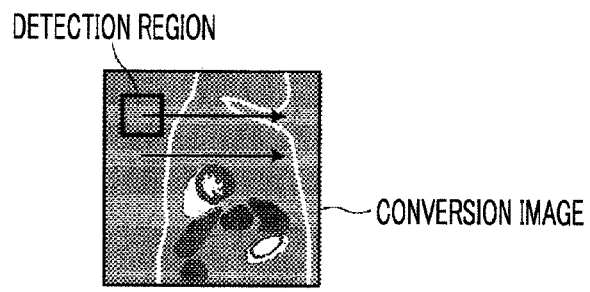
FIG. 4 is a diagram illustrating left ventricle center point extraction processing.

Then, as shown in FIG. 4, a detection region including a pixel of interest at the center in a conversion image is scanned, and a feature amount in the detection region is calculated. This is input to the discriminator obtained in the learning stage, and a discrimination value is calculated. In a case in which the discrimination value exceeds a predetermined threshold value, it is determined that the detection region is a region of the heart including the left ventricle center point.

In order to enable the detection even if the size of the region of the heart in a detection region is different from the size of the heart of the discriminator, the above-described discrimination is performed while changing the resolution of the conversion image.

In a case in which a plurality of candidates for the left ventricle center point are extracted by the left ventricle center point extraction processing described above, the center of gravity of the plurality of candidates is calculated, and the center of gravity is determined as a final left ventricle center point. However, instead of calculating the center of gravity, for example, an evaluation value for each candidate may be calculated based on a predetermined evaluation method, and a final left ventricle center point may be determined from the evaluation value.

Since the left ventricle of the heart has a shape with a pointed tip, the size of the left ventricle region changes with the tomographic location of the tomographic image. Therefore, the resolution of a conversion image to be determined may be changed according to the tomographic location. Alternatively, the left ventricle center point may be extracted from the tomographic image using a plurality of detection regions having different sizes and a discriminator.

For the processing of extracting the left ventricle center point from the conversion image, it is possible to use other known pattern recognition methods without being limited to the method described above. It is one of the characteristic points of the present embodiment to perform conversion based on the equation illustrated in the above Equation (1) in order to stably extract the left ventricle center point from medical images having different pixel values or different contrasts.

Figure 5:
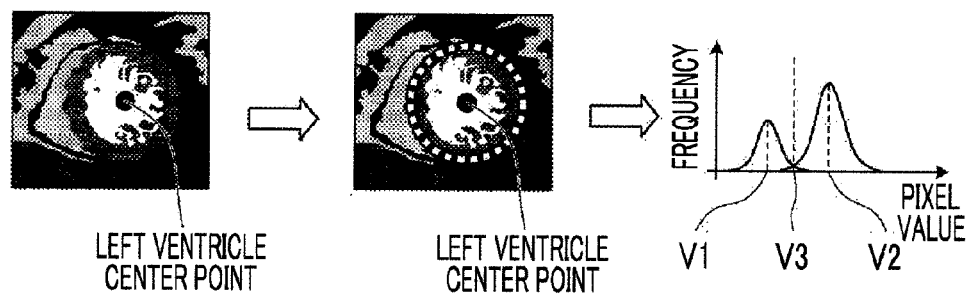
FIG. 5 is a diagram illustrating an embodiment of a method of acquiring the standardization conditions.

Then, the standardization conditions acquisition unit 13 acquires the standardization conditions of the pixel value of the medical image based on some pixel values around the anatomical feature point extracted by the feature point extraction unit 12. Specifically, as shown in FIG. 5, the standardization conditions acquisition unit 13 of the present embodiment sets a circular area near the left ventricle center point in a medical image to be standardized, and collects pixel values in the area to acquire a histogram. In addition, the size of the circular area is determined according to the value set arbitrarily by the user and the resolution with which the feature point has been detected by the feature point extraction unit 12.

In the present embodiment, it is assumed that the pixel value of the ventricle and the pixel value of the myocardium are present in the circular area, and the pixels in the circular area are classified into two classes (distributions). For example, it is possible to use a discriminant analysis method (binarization of Otsu) or the like, and it is possible to obtain average values V1 and V2 of each class. Alternatively, the average values V1 and V2 of each class may also be calculated using a known method, such as a K-means method. Then, values of a and b in the following Equation (2) are determined such that the average values V1 and V2 of the pixel value I(x, y) of each class become standard values V1' and V2' set in advance. By using this equation, input images having different pixel values or different contrasts can be converted into images in which the pixel values of the ventricle and the myocardium are standardized.

$$I_N(x,y)=a*I(x,y)+b \quad (2)$$

In the above explanation, a and b with which the average values V1 and V2 of each class become values set in advance are acquired. However, the present invention is not limited thereto, and c with which a boundary value V3 for classification into respective classes becomes a value set in advance may be acquired, and the following Equation (3) in which the value of c is set may be acquired as standardization conditions.

$$I_N(x,y) = c*I(x,y) \quad (3)$$

Figure 6:
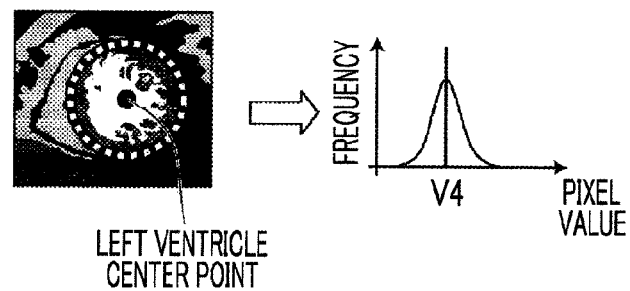
FIG. 6 is a diagram illustrating another embodiment of the method of acquiring the standardization conditions.

In addition, in the above explanation, it is assumed that the pixel value of the ventricle and the pixel value of the myocardium are present in the circular area, and the pixels in the circular area are classified into two classes. However, the present invention is not limited thereto. For example, as shown in FIG. 6, it may be assumed that only the pixel value of the ventricle is present in the circular area by reducing the size of the circular area. In this case, the standardization conditions acquisition unit 13 acquires d with which an average value V4 of each pixel value I(x, y) in the circular area becomes a value set in advance, and acquires the following Equation (4) in which the value of d is set as standardization conditions.

$$I_N(x,y) = d*I(x,y) \quad (4)$$

In addition, in the above explanation, the average values V1, V2, and V4 are calculated. However, the present invention is not limited thereto, and other statistical quantities may be used. For example, a standard deviation may be calculated.

The standardization processing unit 14 performs standardization processing on the medical image based on the standardization conditions acquired by the standardization conditions acquisition unit 13. Specifically, a standardized medical image is generated by calculating $I_N(x, y)$ based on each pixel value I(x, y) of the medical image and one of Equations (2) to (4) described above.

The region extraction processing unit 15 extracts a heart region by performing region extraction processing using the graph cut method for the standardized medical image generated by the standardization processing unit 14. Hereinafter, the region extraction processing using the graph cut method will be described.

Figure 7:
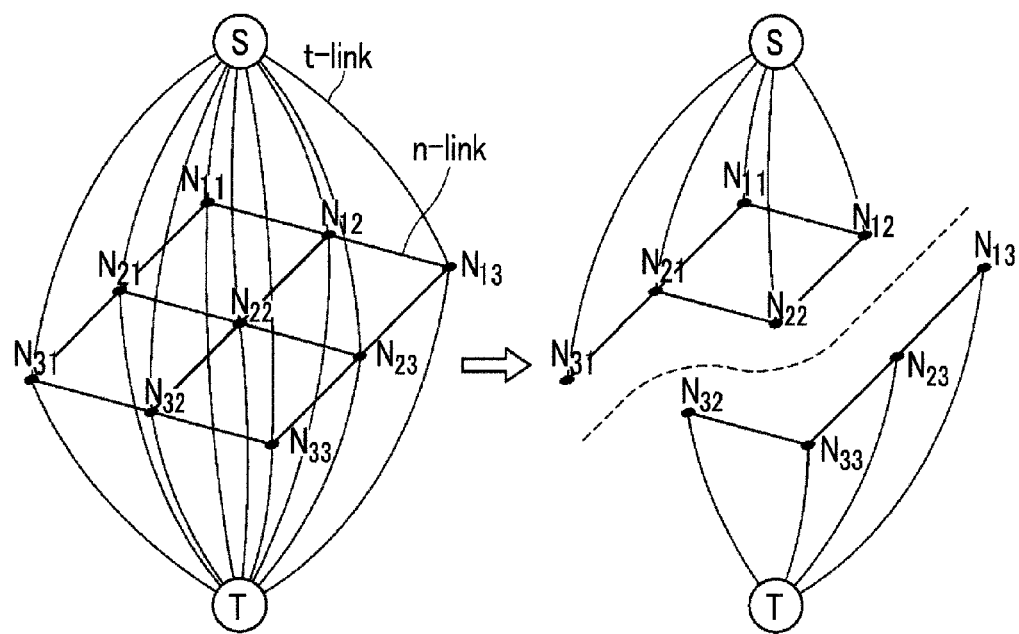
FIG. 7 is a diagram illustrating extraction processing based on a graph cut method.

The region extraction processing unit 15 generates a graphical model including a node $N_{ijk}$ showing each pixel of the standardized medical image, nodes S and T showing a label that each pixel can take (here, a heart region and other regions), an n-link that is a link connecting the nodes of adjacent pixels to each other, a t-link that is a link connecting the node $N_{ijk}$ showing each pixel to the node S showing the heart region or the node T showing a region other than the heart region (refer to the left diagram in FIG. 7. In FIG. 7, in order to facilitate understanding, the division of a two-dimensional region is shown).

Here, n-link expresses a likelihood that adjacent pixels are voxels of the same region, and the likelihood can be calculated, for example, based on the difference between the pixel values of the adjacent pixels. t-link connecting the node $N_{ijk}$ showing each pixel to the node T showing a region other than the left ventricle region expresses a likelihood that the pixel is a pixel included in a region around the left ventricle region. In addition, t-link connecting the node $N_{ijk}$ showing each pixel to the node S showing the left ventricle region expresses a likelihood that the pixel is a pixel included in the left ventricle region.

In addition, n-link or t-link described above can be expressed as a cost function indicating the likelihood.

In the present embodiment, a ventricular region (contrast region) and a myocardial region that form a heart region are separately extracted as heart regions.

When extracting a ventricular region, t-link connecting the node $N_{ijk}$ to the node T showing a region other than the ventricular region can be calculated, for example, based on a result of determination regarding whether or not the pixel value is in a range of pixel values in a region around the ventricular region that have been statistically obtained in advance. In addition, t-link connecting the node $N_{ijk}$ to the node S showing the ventricular region can be calculated, for example, based on a result of determination regarding whether or not the pixel value is in a range of pixel values in the ventricular region that have been statistically obtained in advance.

In addition, by cutting one of two t-links that connect a node showing each pixel to the node S showing a ventricular region and connect a node showing each pixel to the node T showing a region other than the ventricular region and cutting n-link that connects the nodes of adjacent pixels having different labels, division into the ventricular region and a region other than the ventricular region is performed (refer to the right diagram in FIG. 7). In this case, it is possible to realize optimal region division by minimizing the sum of the costs of all oft-link and n-link to be cut. That is, assuming that the cost function of t-link is fv(Xv) and the cost function of n-link is fuv(Xu, Xv), region division is performed so that the sum E(X) of the costs in the following equation is minimized. In addition, the pixel value of the standardized medical image is used in the cost function fv(Xv) of the first term of the following equation.

$$E(X) = \sum_{v \in V} f_v(X_v) + \sum_{(u,v) \in \varepsilon} f_{uv}(X_u, X_v)$$

In addition, when extracting a myocardial region, t-link connecting the node $N_{ijk}$ to the node T showing a region other than the myocardial region can be calculated, for example, based on a result of determination regarding whether or not the pixel value is in a range of pixel values around the myocardial region that have been statistically obtained in advance. In addition, t-link connecting the node $N_{ijk}$ to the node S showing the myocardial region can be calculated, for example, based on a result of determination regarding whether or not the pixel value is in a range of pixel values in the myocardial region that have been statistically obtained in advance.

In addition, by cutting one of two t-links that connect a node showing each pixel to the node S showing a myocardial region and connect a node showing each pixel to the node T showing a region other than the myocardial region and cutting n-link that connects the nodes of adjacent pixels having different labels, division into the myocardial region and a region other than the myocardial region is performed. Also in this case, it is possible to realize optimal region division by minimizing the sum of the costs of all oft-link and n-link to be cut, that is, by calculating the optimal solution.

First, the region extraction processing unit 15 extracts a ventricular region using a graph cut method. Then, the region extraction processing unit 15 extracts a myocardial region from a region excluding the ventricular region using the graph cut method, and acquires a final heart region by combining these regions. A ventricular region and a myocardial region may be extracted simultaneously using a graph cut method of multi-class (refer to Delong, A. Boykov, Y., "Globally optimal segmentation of multi-region objects", ICCV2009 and the like).

As region extraction processing, region extraction processing using an active contour model may be performed without being limited to the region extraction processing based on the graph cut method described above. In the region extraction processing using an active contour model, an evaluation function is defined, and an optimal solution is obtained by calculating the evaluation function while changing the positions of the contour points of a region to be extracted. The region extraction processing using an active contour model is a method already known. For example, it is possible to use a method described in "ETOH: "Survey of Snakes, Active Contour Models", Medical Imaging Technology, Vol. 12, No. 1, pp. 9-15, 1994" or a method described in "M Kass, A Wilin, D Terzopoulos: "Snakes: Active contour models", International Journal of Computer Vision, vol. 1, pp. 321-331, 1988". The evaluation function is defined by three terms for the contour $v(s)=(x(s), y(s))$, as shown in the following equation.

$$E=E_{int}(v(s))+E_{image}(v(s))+E_{con}(v(s))$$

In addition, Eint is a term indicating the internal energy, and is a term to control the smoothness of the contour. Eimage is a term indicating the image energy, and is a term to control the position of the contour to be a position where a brightness change is large. Econ is a term indicating the external energy. For example, in a case in which it is necessary to fix a part of the contour by designation from the outside, it is preferable to add a difference term $(v(s)-p)^2$ between a designated point p and a point $v(s)$ on the contour.

In the above explanation, region extraction processing is performed on the standardized medical image. However, the region extraction processing may be performed by directly adding the conversion equation of standardization conditions to the evaluation function without generating a standardized medical image.

The display control unit 16 displays, on the display 20, the medical image acquired by the medical image acquisition unit 11, a standardized medical image obtained by performing standardization processing on the medical image, the left ventricle region image extracted by the region extraction processing unit 15, and the like.

Here, the display control unit 16 of the present embodiment can perform gradation display of the standardized medical image obtained by performing standardization processing. During the gradation display, the display control unit 16 sets a window width (WW) or a window level (WL) based on the standardization conditions described above. The window width (WW) and the window level (WL) are set in advance so as to correspond to the size of the pixel value and the brightness of the standardized medical image.

In addition, the display control unit 16 can perform color display of the standardized medical image. During the color display, the display control unit 16 sets a color map based on the standardization conditions described above. The color map is set in advance so as to correspond to the size of the pixel value and the color of the standardized medical image.

The input device 30 receives an input of predetermined information of the user. For example, the input device 30 is formed by a pointing device, such as a keyboard or a mouse.

Figure 8:
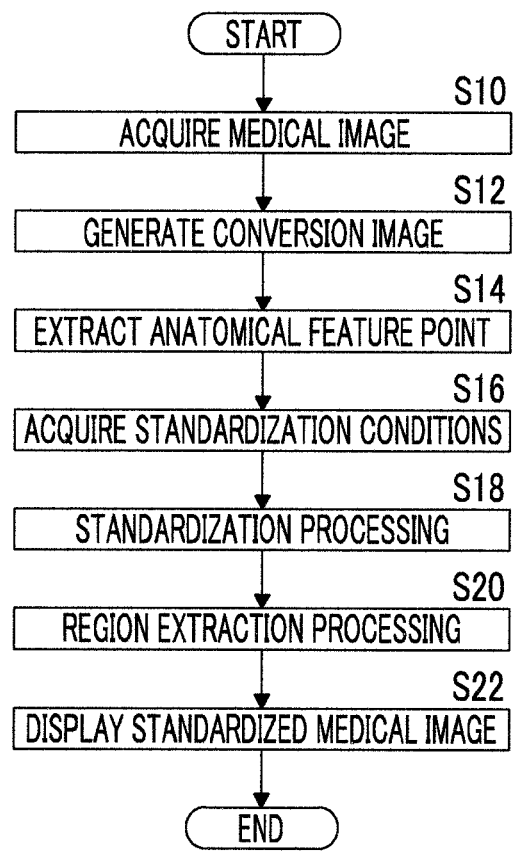
FIG. 8 is a flowchart illustrating the operation of an embodiment of the medical image processing device, the operation method therefor, and the medical image processing program of the present invention.

Next, the operation of the medical image diagnosis support system using an embodiment of the present invention will be described with reference to the flowchart shown in FIG. 8.

First, identification information of a subject is input in the input device 30, and the medical image acquisition unit 11 of the medical image processing device 10 reads and acquires a medical image corresponding to the input identification information of the subject from the medical image storage server 40 (S10). Here, it is assumed that a medical image captured by the MRI apparatus is read and acquired as a medical image as described above.

The medical image acquired by the medical image acquisition unit 11 is input to the feature point extraction unit 12, and the feature point extraction unit 12 generates a conversion image by performing the above-described conversion processing on the medical image (S12). Then, the feature point extraction unit 12 extracts a left ventricle center point from the conversion image as an anatomical feature point (S14).

Then, the medical image and the position information of the left ventricle center point are input to the standardization conditions acquisition unit 13, and the standardization conditions acquisition unit 13 acquires the standardization conditions of the pixel value of the medical image based on some pixel values around the left ventricle center point (S16).

The standardization conditions acquired by the standardization conditions acquisition unit 13 are input to the standardization processing unit 14, and the standardization processing unit 14 generates a standardized medical image by performing standardization processing on the medical image based on the standardization conditions (S18).

The standardized medical image is input to the region extraction processing unit 15, and the region extraction processing unit 15 extracts a left ventricle region from the standardized medical image using a graph cut method (S20).

Then, the standardized medical image, the image of the left ventricle region, and the like are displayed on the display by the display control unit 16 (S22).

According to the medical image diagnosis support system of the embodiment described above, an anatomical feature point included in a medical image is extracted, the standardization conditions of the pixel value of the medical image are acquired based on some pixel values around the anatomical feature point, and the medical image is standardized based on the standardization conditions. Therefore, it is possible to accurately extract an anatomical region from the medical image and to reduce a variation in the pixel values or the contrast of each medical image. In addition, since the standardization conditions are acquired based on some pixel values around the anatomical feature point, it is possible to acquire the more appropriate standardization conditions corresponding to the anatomical structure.

In the embodiment described above, a case in which an MR image is acquired as a medical image has been described. However, applications to other images, such as an ultrasound image, are also possible.

In the embodiment described above, a case has been described in which a tomographic image is acquired as a medical image and the standardization conditions of the tomographic image are acquired. However, a three-dimensional image formed of a plurality of tomographic images may be acquired as a medical image, and the standardization conditions of the three-dimensional image may be acquired. Hereinafter, a method of acquiring the standardization conditions of a three-dimensional image including the heart will be described.

First, a conversion image of each tomographic image is generated by performing conversion processing on each tomographic image, which forms the three-dimensional image, in the same manner as in the case of the tomographic image described above. Then, a left ventricle center point is extracted from each conversion image as an anatomical feature point in the same manner as described above. Then, the centerline of the left ventricle is acquired by linearly approximating the left ventricle center point extracted in each conversion image.

Then, for each tomographic image, each circular area having an intersection with the centerline of the left ventricle as its center is set, and pixel values in the circular area are collected. Then, in the same manner as described above, standardization conditions for each tomographic image are acquired, and a standardized tomographic image is generated by performing standardization processing based on the standardization conditions.

Then, a left ventricle region is extracted by performing region extraction processing using a graph cut method for a standardized three-dimensional image formed of a plurality of standardized tomographic images. The image of the left ventricle region or the standardized three-dimensional image is displayed on the display 20. In this case, however, as described above, the window width (WW) or the window level (WL) or the color map set in advance so as to correspond to the size of the pixel value of the standardized three-dimensional image is used.

In the above explanation, the standardization conditions are acquired for each tomographic image that forms a three-dimensional image. However, a set of standardization conditions may be acquired for a three-dimensional image without being limited to the above. Specifically, for example, a three-dimensional area having a cylindrical shape as shown in FIG. 9 may be set around the centerline acquired by linearly approximating the left ventricle center point, and a set of standardization conditions may be acquired by collecting and analyzing the pixel values in the three-dimensional area.

Figure 9:
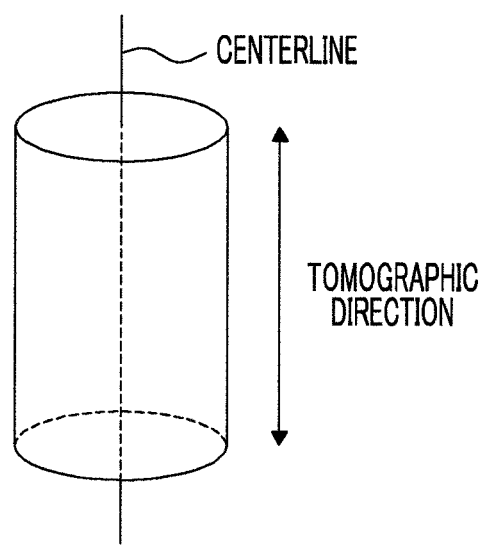
FIG. 9 is a diagram showing an example of the three-dimensional area set when generating a histogram.
Figure 10:
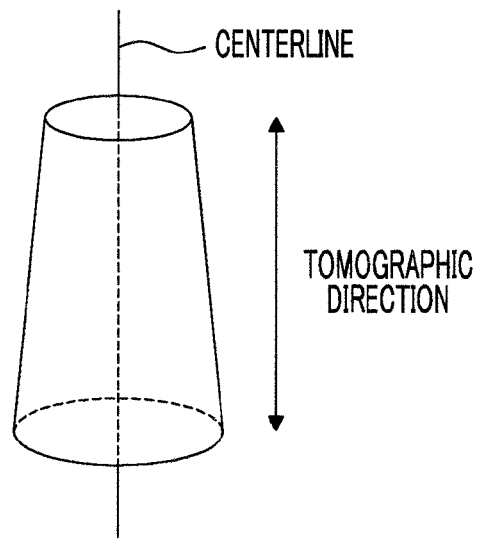
FIG. 10 is a diagram showing another example of the three-dimensional area set when generating a histogram.

The shape of the three-dimensional area is not limited to the cylindrical shape shown in FIG. 9, and a truncated cone shape shown in FIG. 10 may be used since the left ventricle of the heart has a pointed tip. That is, an area for collecting the pixel values of the histogram may be set according to the shape of the target organ. Without being limited to the case of acquiring a set of standardization conditions for the three-dimensional image, the size of the circular area may also be changed according to the tomographic location of each tomographic image in a case of acquiring the standardization conditions by setting the circular area for each tomographic image.

Figure 11:
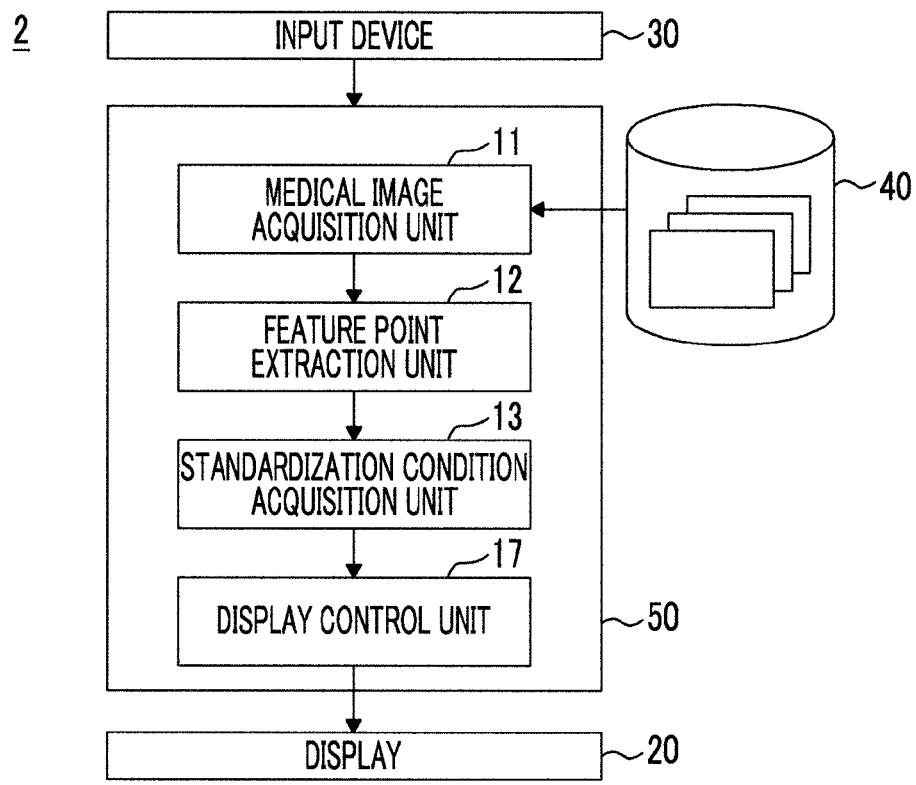
FIG. 11 is a block diagram showing the schematic configuration of a medical image diagnosis support system using another embodiment of the medical image processing device, the operation method therefor, and the medical image processing program of the present invention.

In the embodiment described above, a standardized tomographic image or a standardized three-dimensional image is generated by performing standardization processing on a medical image based on the standardization conditions. However, these images do not necessarily need to be generated. FIG. 11 shows the configuration of a medical image diagnosis support system 2 that generates neither a standardized tomographic image nor a standardized three-dimensional image.

In a medical image processing device 50 of the medical image diagnosis support system 2 shown in FIG. 11, the standardization conditions acquired by the standardization conditions acquisition unit 13 are input to a display control unit 17. Since the setting of the window width (WW) and the window level (WL) described above is also linear conversion similar to the standardization processing based on the standardization conditions, the display control unit 17 generates a display image by calculating a linear conversion equation including both the standardization conditions and the setting of the window width (WW) and the window level (WL) and performing processing based on the linear conversion equation directly on the medical image.

Then, the display control unit 17 displays the display image, which has been generated directly from the medical image as described above, on the display 20.

In the embodiment described above, only the region of the left ventricle is extracted. However, the region of the right ventricle may be further extracted.

In the explanation of the above embodiment, the center point of the left ventricle is extracted as an anatomical feature point, but the present invention is not limited thereto. For example, in the case of the heart, the apical point of the heart, a point where the apices of respective valves forming a tricuspid valve or an aortic valve intersect with each other, and the like may be used. Other than the heart, an aorta center point, an eye center point, a spinal cord center point, a spine center point, and the like may be used. For example, various known anatomical feature points, such as an anatomical feature point described in U.S. Pat. No. 7,599,539B, can be used.

In addition, images standardized based on the anatomical feature points described above can be used for the region extraction of the aorta, eye, spinal cord, spine, and the like.

In a case of acquiring a four-dimensional image, which is obtained by adding the time axis to the three-dimensional image of the heart, as a medical image, standardization conditions may be acquired based on the three-dimensional image of the heart in the end-diastole phase, and a standardized three-dimensional image, a display image, or the like may be generated using the standardization conditions for the three-dimensional image of the heart in other phases. Using the result of extraction of the left ventricle region from the standardized three-dimensional image in the end-diastole phase, the left ventricle region may be extracted from a three-dimensional image before standardization processing or a standardized three-dimensional image in other phases. Since the method of extracting the left ventricle region in other phases based on the extraction result of the left ventricle region in the end-diastole phase is already known, the explanation thereof will be omitted.

What is claimed is:

1. A medical image processing device, comprising:
a processor configured to:
extract an anatomical feature point included in a medical image based on the medical image;
acquire standardization conditions of pixel values of the medical image based on some pixel values around the anatomical feature point among the pixel values of the medical image; and
perform region extraction processing for extracting an anatomical region included in the medical image based on the standardization conditions and the medical image,
wherein the processor generates a conversion image by performing conversion processing on each pixel value of the medical image based on a statistical quantity that is calculated based on pixel values around each pixel value, and extracts the anatomical feature point based on the conversion image, and
wherein the conversion processing calculates an average value Mlocal and a standard deviation SDlocal from the pixel values of pixels surrounding the each pixel and calculates each pixel value Ic(x, y) of the conversion image by using the following Equation $$Ic(x,y)=(I(x,y)-M\text{local})\times Const/SD\text{local}$$

wherein x, y represent coordinate values of the each pixel of the medical image and Const is a constant set in advance.

2. The medical image processing device according to claim 1,
wherein the processor acquires pixel values of a pixel group around the anatomical feature point, acquires a statistical quantity of the pixel values of the pixel group, and acquires standardization conditions based on the statistical quantity.

3. The medical image processing device according to claim 2,
wherein the processor classifies the pixel values of the pixel group into a plurality of groups, acquires a statistical quantity of each of the groups, and acquires the standardization conditions based on the statistical quantity.

4. The medical image processing device according to claim 2,
wherein the processor acquires the standardization conditions in which the statistical quantity of the pixel values of the pixel group is a value set in advance.

5. The medical image processing device according to claim 1,
wherein the processor acquires pixel values of a pixel group around the anatomical feature point, acquires a boundary value for classifying the pixel group into a plurality of groups, and acquires the standardization conditions based on the boundary value.

6. The medical image processing device according to claim 5,
wherein the anatomical feature point is a left ventricle center point; and
wherein the boundary value is the value that divides into the pixel value of a ventricle and the pixel value of a myocardium.

7. The medical image processing device according to claim 6, wherein the processor performs standardization processing on the medical image using the standardization conditions,
wherein the standardization processing standardizes the pixel values such that an average of the pixel value included in each group of the plurality of groups becomes a standard value that is set in advance.

8. The medical image processing device according to claim 1,
wherein the processor performs the region extraction processing by setting an evaluation function based on the standardization conditions and the medical image and calculating an optimal solution of the evaluation function.

9. The medical image processing device according to claim 1, wherein the processor performs standardization processing on the medical image using the standardization conditions.

10. The medical image processing device according to claim 9, further comprising:
a display controller that displays a medical image having been subjected to the standardization processing.

11. The medical image processing device according to claim 10,
wherein the display controller sets a window width and a level value based on the standardization conditions.

12. The medical image processing device according to claim 9,
wherein the standardization processing standardizes the pixel values such that an average of the pixel value included in each group of the plurality of groups becomes a standard value that is set in advance.

13. The medical image processing device according to claim 1, further comprising:
a display controller that generates a display image by performing processing including both the standardization conditions and display conditions directly on the medical image and displays the display image.

14. The medical image processing device according to claim 1, wherein the medical image is captured by a magnetic resonance imaging (MRI) apparatus.

15. An operation method of a medical image processing device including a processor, comprising:
extracting an anatomical feature point included in a medical image based on the medical image;
acquiring standardization conditions of pixel values of the medical image based on some pixel values around the anatomical feature point among the pixel values of the medical image; and
performing region extraction processing for extracting an anatomical region included in the medical image based on the standardization conditions and the medical image,
wherein a conversion image is generated by performing conversion processing on each pixel value of the medical image based on a statistical quantity that is calculated based on pixel values around each pixel value, and extracts the anatomical feature point based on the conversion image, and
wherein the conversion processing calculates an average value Mlocal and a standard deviation SDlocal from the pixel values of pixels surrounding the each pixel and calculates each pixel value Ic(x, y) of the conversion image by using the following Equation $Ic(x,y)=(I(x,y)-Mlocal) \times Const/SDlocal$ wherein x, y represent coordinate values of the each pixel of the medical image and Const is a constant set in advance.

16. A non-transitory computer-readable recording medium having stored therein a medical image processing program that causes a computer to:
extract an anatomical feature point included in a medical image based on the medical image;
acquire standardization conditions of pixel values of the medical image based on some pixel values around the anatomical feature point among the pixel values of the medical image; and
perform region extraction processing for extracting an anatomical region included in the medical image based on the standardization conditions and the medical image,
wherein the processor generates a conversion image by performing conversion processing on each pixel value of the medical image based on a statistical quantity that is calculated based on pixel values around each pixel value, and extracts the anatomical feature point based on the conversion image, and
wherein the conversion processing calculates an average value Mlocal and a standard deviation SDlocal from the pixel values of pixels surrounding the each pixel and calculates each pixel value Ic(x, y) of the conversion image by using the following Equation $Ic(x,y)=(I(x,y)-Mlocal) \times Const/SDlocal$ wherein x, y represent coordinate values of the each pixel of the medical image and Const is a constant set in advance.

* * * * *